(12) United States Patent
Ortega Cruz et al.

(10) Patent No.: US 8,425,694 B2
(45) Date of Patent: Apr. 23, 2013

(54) IMPLANT AND PROCESS FOR PRODUCING IT, IN PARTICULAR MODIFICATION OF ITS SURFACE

(75) Inventors: Luis Alfonso Ortega Cruz, Selzach (CH); Falko Schlottig, Fullinsdorf (CH)

(73) Assignee: Thommen Medical AG, Waldenburg (CH)

( * ) Notice: Subject to any disclaimer, the term of this patent is extended or adjusted under 35 U.S.C. 154(b) by 124 days.

(21) Appl. No.: 12/809,626

(22) PCT Filed: Dec. 12, 2008

(86) PCT No.: PCT/CH2008/000527
§ 371 (c)(1),
(2), (4) Date: Jun. 21, 2010

(87) PCT Pub. No.: WO2009/079805
PCT Pub. Date: Jul. 2, 2009

(65) Prior Publication Data
US 2010/0274361 A1    Oct. 28, 2010

(30) Foreign Application Priority Data
Dec. 20, 2007  (CH) ..................................... 1982/07

(51) Int. Cl.
*A61F 2/28* (2006.01)
(52) U.S. Cl.
USPC ...................... 148/272; 433/201.1; 623/23.56
(58) Field of Classification Search .................. 148/272; 623/23.56; 433/201.1
See application file for complete search history.

(56) References Cited

U.S. PATENT DOCUMENTS

| 6,818,332 B1 | 11/2004 | Niedhart et al. |
| 2001/0036530 A1 | 11/2001 | Noda et al. |

FOREIGN PATENT DOCUMENTS

| DE | 19858501 A1 | 6/2000 |
| WO | 2006/131010 A2 | 12/2006 |

*Primary Examiner* — Lois Zheng
(74) *Attorney, Agent, or Firm* — Sughrue Mion, PLLC

(57) ABSTRACT

A process for producing a ceramic implant which is structured on the surface at least in the region in contact with bone and/or tissue is described. The process is characterized in that the ceramic implant after shaping and sintering is, in the region to be structured, I. reduced to the corresponding metal on the surface; II. the essentially metallic surface is subsequently subjected to a structuring surface treatment; III. the structure surface is oxidized. Furthermore, implants which have been provided with a topological structure on the surface by means of this process are described.

22 Claims, 11 Drawing Sheets a)

b)

a)

b)

a)

b)

a)

b)

IMPLANT AND PROCESS FOR PRODUCING IT, IN PARTICULAR MODIFICATION OF ITS SURFACE

TECHNICAL FIELD

The present invention relates to a process for producing a ceramic implant which is structured on the surface, at least in the area exposed to bone and/or tissue. Implants are also described and claimed whose surface has been provided with a topological structure using this process.

PRIOR ART

There are numerous implants that for many years have been introduced as replacement material or as building material into the human body. In the field of so-called bone implants, that is to say those implants that are introduced at least partly into the bone, for example joint implants, spinal implants, dental implants, the main focus has been on implants made of metal or of ceramic. One or other material is used depending on the required material properties and on the preferences of the patient.

To ensure that implants become firmly incorporated in the bone and/or the adjoining tissue, it is customary either to modify the surface of the implants or to apply a coating to the surface of the implants. In the first case, this involves providing the surface with a topological structure, for example a roughness within a defined microscopic range, such that the tissue or the bone is able to build an anchor to the implant. In the second case, this involves providing the surface with coatings that promote or activate the incorporation of the implant, for example with active substances that stimulate the adjoining tissue to accelerate the anchoring or the process of incorporation.

In connection with implants, there are various processes for producing a structured, i.e. rough, surface. On the one hand, this can be done by an abrasive blasting treatment, for example by blasting with sand of a defined grain size (mesh). On the other hand, this can be done by a chemical treatment, for example by a treatment that partially attacks and dissolves or modifies the surface. In the case of metallic implants, EP 0 388 576, for example, describes a process in which the implant is exposed to concentrated acid, if appropriate after preliminary treatment by sandblasting. In the case of ceramic implants, WO 00/37121, for example, describes a process in which the surface is treated in an alkaline solution.

In general, depending on the base material used (metal/ceramic), different processes are known for treating the surface in order to create a structuring, and these different processes also give rise to different structures on the surfaces of the implants.

SUMMARY OF THE INVENTION

The object of the invention is therefore to make available an alternative process for structuring the surfaces of ceramic implants. The process should be as versatile as possible and should, by adjustment of the process parameters, be able to create the widest possible variety of topologies. The invention therefore relates to an improvement of a process for producing a ceramic implant which is structured on the surface, at least in the area exposed to bone and/or tissue, and to corresponding implants, in particular dental implants.

This object is achieved by virtue of the fact that, after it has been shaped and possibly already sintered, the ceramic implant, in the area to be structured I is reduced to the corresponding metal on the surface;
II the substantially metallic surface is then subjected to a structuring surface treatment;
III the structured surface is oxidized.

In other words, one of the main aspects of the invention is the discovery that it is unexpectedly possible to first of all reduce a ceramic implant to the metallic form in the surface area (oxidation state 0), that it is then possible to carry out all processes known from the field of metallic implants in order to structure the surface on this uppermost metallic layer, and that the metallic surface layer thus structured can then be oxidized back again. In this way, the many known processes for structuring a metallic surface can be used in step II and, for example, taken from the literature. Thereafter, however, as a result of step III, it is possible to obtain a similar structure, but in many processes not exactly the same structure, as in the treatment of a metallic implant only with step II, that is to say novel structurings are made available on the surface.

An important advantage of the proposed process is that, because of the extensive knowledge of the structuring of metallic surfaces, this knowledge can be transferred at least in part to the structuring of ceramic implants. It is thus possible, almost to any desired extent, to create a suitable structuring of the surface of a ceramic implant, depending on the process chosen in step II (if appropriate in combination with a preliminary or subsequent structuring) and depending on the settings of the parameters.

An important advantage of the proposed process is that the surface of the ceramic implant is created using the material of the implant (an autochthonous structure as it were) and not with the aid of coating processes. The latter generally lead to problems with the adherence of the coating, which problems can be completely ruled out in the novel process proposed here, for example because step I does not involve the formation of a conventional layer with a smooth boundary surface to the ceramic material, but instead a strongly indented surface modification, which is tailored to the strength and the porosity of the worked material and which accordingly also ensures an intimate union in each stage of the process.

The ceramic surface (typically $ZrO_2$ and mixtures of $ZrO_2$ and $Al_2O_3$) is therefore first of all reduced to the metal in a defined environment. The metal surface obtained is structured by etching processes or other methods. The structured metallic surface is oxidized in a defined environment. This results in the desired structured ceramic implant surface.

A first embodiment of the proposed process is characterized in that the ceramic implant, before and/or while being shaped and/or sintered, has already been subjected to a structuring of the surface (e.g. structuring of the surface of the green body, or also structuring or coating of the mold for the shaping with spacers).

Alternatively or in addition, it is also possible that the ceramic implant, after being shaped and/or sintered, but before being treated in steps I-III, has already been subjected to a structuring of the surface.

The preliminary structuring of the surface of the ceramic implant can in other words be done, for example, by surface structuring of the green body before the sintering. However, it can also be done by using a mold in the shaping step, which mold is structured on the inside or has spacers. It can equally be done by surface structuring of the sintered ceramic implant (the latter can also have already been subjected to an additional grinding treatment or another process). These stated structurings in the surface can be used alternatively or together. Generally, the structuring in this process can preferably involve a mechanical treatment such as abrasive blasting and/or a chemical treatment such as treatment with acid, treatment with alkaline solution, treatment with molten salt. The conditions in the chemical treatment are analogous here to the ones described further below for step II.

Both for the structuring of the surface of the green body and also the surface of the sintered implant, it is preferable to use either a single abrasive blasting agent or, better still, a mixture of two abrasive blasting agents with different grain size distribution and/or of different material. Thus, according to another preferred embodiment, the abrasive blasting treatment can be, for example, an abrasive blasting treatment with simultaneous and/or consecutive treatment with two abrasive blasting agents of different mean grain size. Thus, preferably as a mixture with a proportion of an abrasive blasting agent of coarse grain size in the range of 80-180 mesh and a proportion of a small grain size in the range of 300-450 mesh, and the abrasive blasting agent can be sand and/or organic material such as fruit kernels. In this connection, fine sand and coarse fruit kernels are particularly preferred. The use of a mixture of two abrasive blasting agents with different grain size distribution leads to formation of a bimodal porosity distribution, that is to say a macrostructure which is superposed by a microstructure. With regard to the incorporation behavior of the implant, such a surface structure is of great advantage in combination with the downstream treatment in steps I-III.

Another preferred embodiment is characterized in that the reduction in step I is carried out under a reducing gas atmosphere, preferably under a hydrogen atmosphere. This reduction under a gas atmosphere is preferably carried out at a high temperature, typically above 500° C., preferably above 800° C., particularly preferably in the range of 1000° C.-1400° C. Moreover, the treatment under a reducing gas atmosphere is preferably carried out for a duration of at least 10 minutes, preferably at least 30 minutes, particularly preferably in the range of 40 minutes to 20 hours.

Alternatively or in addition, it is possible that the reduction in step I is carried out using graphite, preferably in the context of the sintering, particularly preferably as hot isostatic pressing (HIP) in the presence of graphite. The graphite, particularly in the HIP process, is preferably used as reducing agent at a temperature above 500° C., preferably above 1000° C., particularly preferably in the range of 1200° C.-1800° C. The reduction using graphite preferably takes place for a duration of at least 10 minutes, preferably at least 30 minutes, particularly preferably in the range of 40 minutes to 20 hours. It is preferably done at a pressure above 200 bar, preferably above 500 bar, particularly preferably in the range of 800 bar to 1500 bar.

According to another embodiment, in step II the substantially metallic surface is exposed, in the area to be structured, to a treatment with acid, in particular with the aid of concentrated acid. The treatment with acid is preferably carried out using a mixture of strong acids, for example using a mixture of hydrochloric acid and/or sulfuric acid and/or nitric acid. For example, a mixture of 50% hydrochloric acid (ca. 30% strength) and 25% sulfuric acid (ca. 95-97% strength) is preferably used. Generally, the treatment with acid is carried out preferably at a temperature above 80° C., particularly preferably at a temperature above 100° C., for example at 120° C. The treatment with acid takes place by preference for a duration of at least 60 minutes, particularly preferably at least 100 minutes, preferably in the range of 110-400 minutes.

Alternatively or in addition, it is possible, in step II, for the substantially metallic surface to be subjected, in the area to be structured, to a treatment in a molten salt. This is preferably done with the aid of alkali metal and/or alkaline earth metal chlorides and/or hydroxides. It is preferably done with a mixture of lithium hydroxide and sodium hydroxide (preferably in the ratio 1:2 to 2:1). The treatment in a molten salt is carried out preferably at a temperature above 80° C., particularly preferably at a temperature above 100° C. The treatment in the molten salt preferably takes place for a duration of at least 20 minutes, particularly preferably at least 40 minutes, preferably in the range of 80-400 minutes.

Another preferred embodiment of the invention is characterized in that, in step III, the surface-structured implant is kept under an oxidizing gas atmosphere, preferably air, at a temperature above 800° C., preferably above 1000° C., particularly preferably in the range of 1000° C.-1500° C. The treatment under this oxidizing atmosphere preferably takes place for a duration of at least 60 minutes, preferably for a duration of at least 100 minutes, particularly preferably for a duration in the range of 120-600 minutes. Other oxidation processes can also be used, for example acid oxidation, plasma oxidation or the like, and which of these processes are especially suitable for a specific type of ceramic can be ascertained by tests carried out by a person skilled in the art.

According to a preferred embodiment, the process is used for the structuring of a ceramic implant based on metal oxide, preferably based on alumina and/or based on zirconia and/or based on silicon nitride, particularly preferably on yttria-stabilized tetragonal zirconia polycrystals (Y-TZP).

Furthermore, the present invention relates to a ceramic implant, particularly a dental implant, which can be produced or is produced by a process as described above. The implant is preferably based on zirconia, particularly preferably based on yttria-stabilized tetragonal zirconia polycrystals (Y-TZP).

Furthermore, the present invention relates to the use of a process as described above for structuring the surface of an implant, preferably of a dental implant, at least in the area exposed to the bone and/or the gum.

BRIEF DESCRIPTION OF THE DRAWINGS

The invention is explained in more detail below on the basis of illustrative embodiments and with reference to the figures. All the figures show scanning electron microscope (SEM) images of the surfaces of examples that are described in detail below. Apparatus: Leica Cambridge S-360 scanning electron microscope. All the images were taken at a high voltage of 20 kV in a high vacuum. The samples were first of all sputtered with ca. 10 nm of gold in a PVC process.

PREFERRED EMBODIMENTS OF THE INVENTION

Many different surface structurings were performed in order to document the versatility of the various structures. The reduction was mainly carried out with hydrogen and with graphite, and the treatment of the metallic surface was carried out with acid and with molten salt. The green body was in some cases already structured, or the mold for the sintering was structured on the surface in such a way that the resulting shaped body had a surface structuring. The parameters such as temperature, duration of treatment, etc., were varied in order to document how versatile the resulting structure can be made. Unless otherwise specified, the abrasive blasting agent used in the abrasive blasting treatment is alumina $Al_2O_3$ with the indicated particle size.

The roughness measurements of the surface of the implant were in each case measured at the thread root. Devices, methods and measurement parameters: confocal microscopy 3 dimensional. White light microscopy CLA (Chromatic Light Aberration) ALTI SURF 500. Optical probe range: 300 μm. Lateral resolution: <2 μm. Z resolution 10 nm. Gaussian filter with cut-off=32 μm, Sz, Sds and SSc parameters are defined as per EUR15178N report. ISO 13565 for RK parameters. All measured values in μm.

Procedure 1

Reduction of the Ceramic Surface in Hydrogen, Etching of the Metallized Surface with Acid

Example 1

Figure 1:
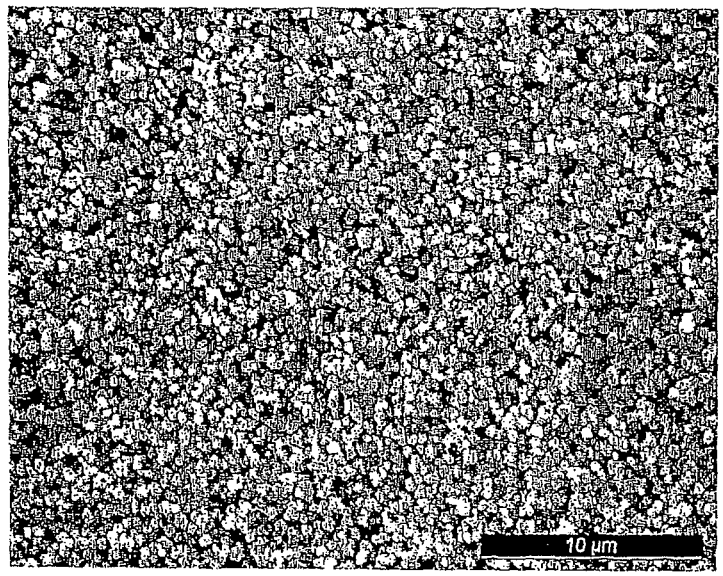
FIG. 1 in a) shows the structured surface of the implant according to example 1 below before oxidation, and in b) the surface oxidized at 1350° C. for 140 min so the resulting structured surface of the oxidized implant.
Figure 1:
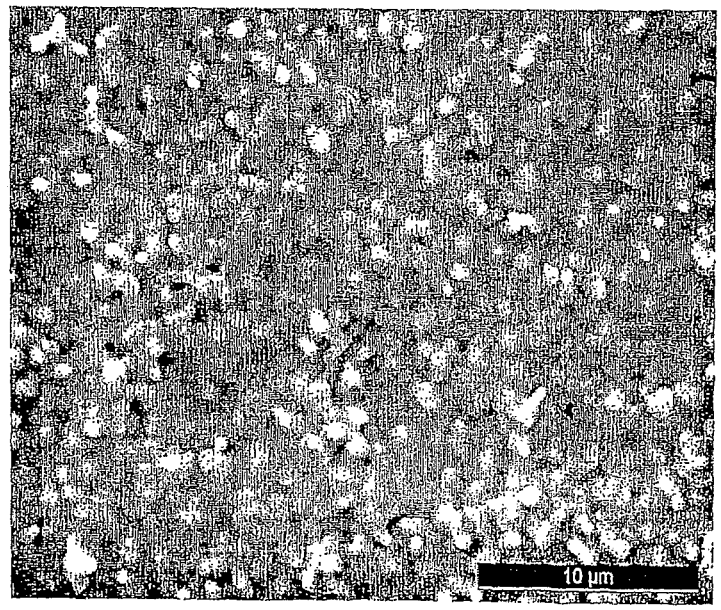

A green body in the form of a cylindrical tooth implant measuring 10 mm in length and 4 mm in diameter was injected from yttria-stabilized zirconia powder (Y-TZP, CIM process). The green body was not sandblasted. After the injection and sintering, the surface of the part was reduced in H2 atmosphere at 1200° C. for 60 min (step I). The surface thus metallized was etched with an acid mixture (50% HCl (32% strength)/25% $H_2SO_4$ (95-97% strength)) at 140° C. for 120 min (step II). The resulting structured surface of the implant before oxidation is shown in FIG. 1a. The surface thus structured was oxidized at 1350° C. for 140 min (step III). The resulting structured surface of the oxidized implant is shown in FIG. 1b. The measured roughness values were as follows:

| Sa | Sq | St | Sk | Rt | Rq | Ra |
|---|---|---|---|---|---|---|
| 0.665 | 0.805 | 5.21 | 0.399 | 1.62 | 0.191 | 0.052 |

Example 2

Figure 2:
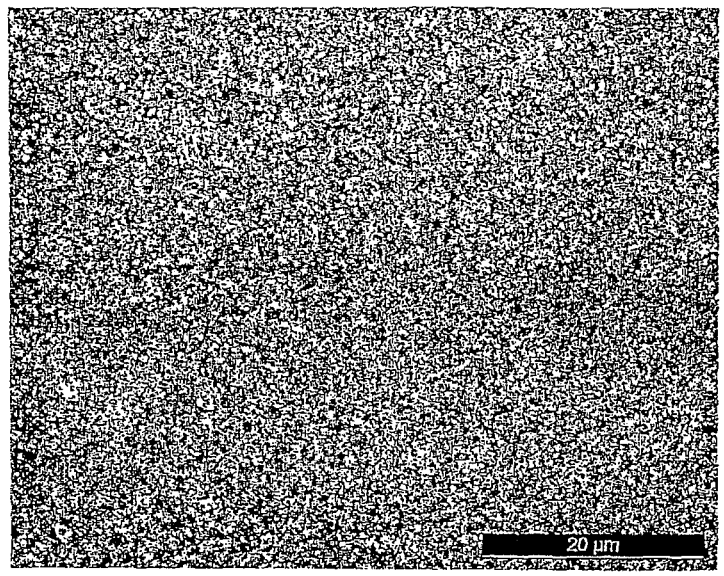
FIG. 2 in a) and b) (different magnifications) shows the resulting oxidized structured surface of the implant according to example 2.
Figure 2:
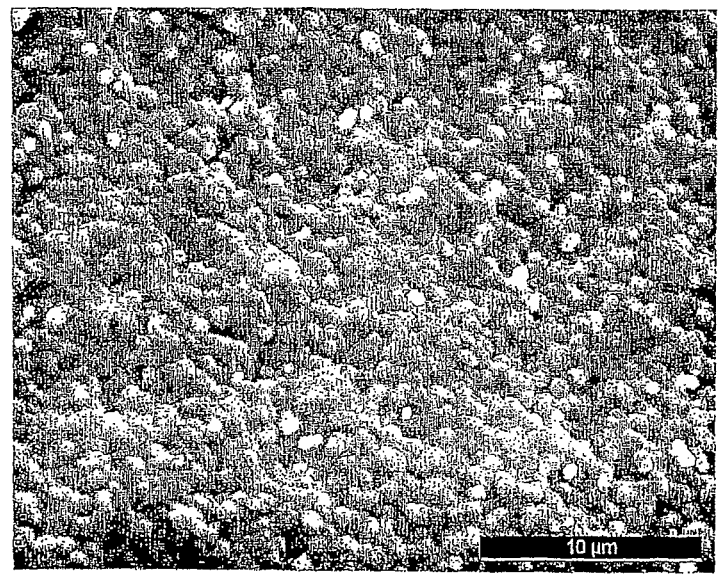

A green body in the form of a cylindrical tooth implant measuring 10 mm in length and 4 mm in diameter was injected from yttria-stabilized zirconia powder (Y-TZP, CIM process). The green body was not sandblasted. After the injection and sintering, the surface of the part was reduced in H2 atmosphere at 1200° C. for 60 min. The surface thus metallized was etched with an acid mixture (50% HCl (32% strength)/25% $H_2SO_4$ (95-97% strength)) at 140° C. for 120 min. The surface thus structured was oxidized at 1200° C. for 140 min. The resulting structured surface of the implant is shown in FIGS. 2a and 2b. The measured roughness values were as follows:

| Sa | Sq | St | Sk | Rt | Rq | Ra |
|---|---|---|---|---|---|---|
| 0.665 | 0.805 | 5.21 | 0.399 | 1.62 | 0.191 | 0.052 |

Example 3

Figure 3:
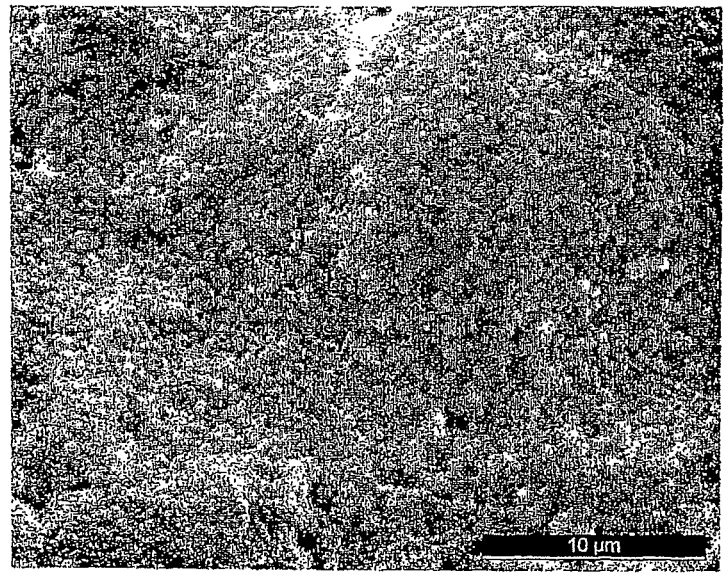
FIG. 3 shows resulting oxidized structured surface of the implant according to example 3.

A green body in the form of a cylindrical tooth implant measuring 10 mm in length and 4 mm in diameter was injected from yttria-stabilized zirconia powder (Y-TZP, CIM process). The green body was not sandblasted. However, the injection tool was modified by means of erosion, such that the green body has a macrostructure after the injection. Thereafter, the surface of the injected green body was reduced in H2 atmosphere at 1200° C. for 60 min. The surface thus metallized was etched with an acid mixture (50% HCl (32% strength)/25% $H_2SO_4$ (95-97% strength)) at 110° C. for 300 min. The surface thus structured was oxidized at 1200° C. for 140 min. The resulting structured surface of the implant is shown in FIG. 3. The measured roughness values were as follows:

| Sa | Sq | St | Sk | Rt | Rq | Ra |
|---|---|---|---|---|---|---|
| 2.52 | 3.31 | 28 | 1.34 | 7.01 | 0.72 | 0.567 |

Example 4

Figure 4:
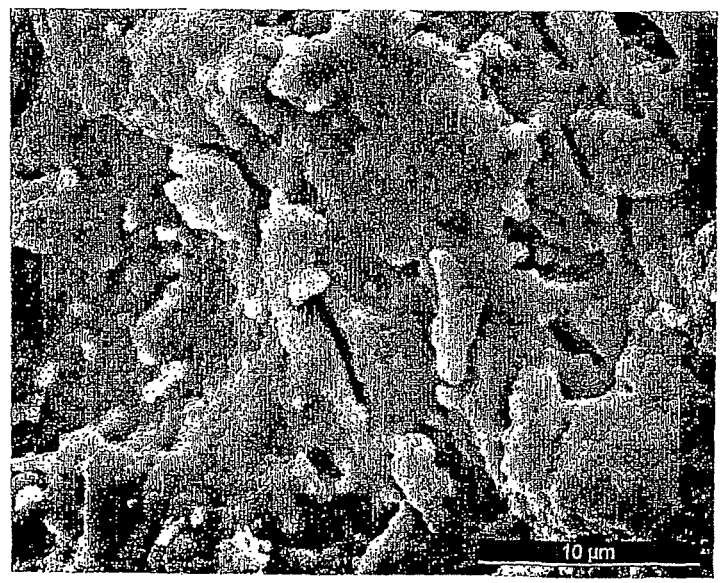
FIG. 4 shows resulting oxidized structured surface of the implant according to example 4.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 120-mesh particle size. Thereafter, the surface of the injected and sintered part was reduced in H2 atmosphere at 1200° C. for 60 min. The surface thus metallized was etched with an acid mixture (50% HCl (32% strength)/25% $H_2SO_4$ (95-97% strength)) at 110° C. for 300 min. The surface thus structured was oxidized at 1200° C. for 140 min. The resulting structured surface of the implant is shown in FIG. 4. The measured roughness values were as follows:

| Sa | Sq | St | Sk | Rt | Rq | Ra |
|---|---|---|---|---|---|---|
| 4.13 | 5.12 | 35.8 | 0.99 | 5.35 | 0.534 | 0.429 |

Example 5

Figure 5:
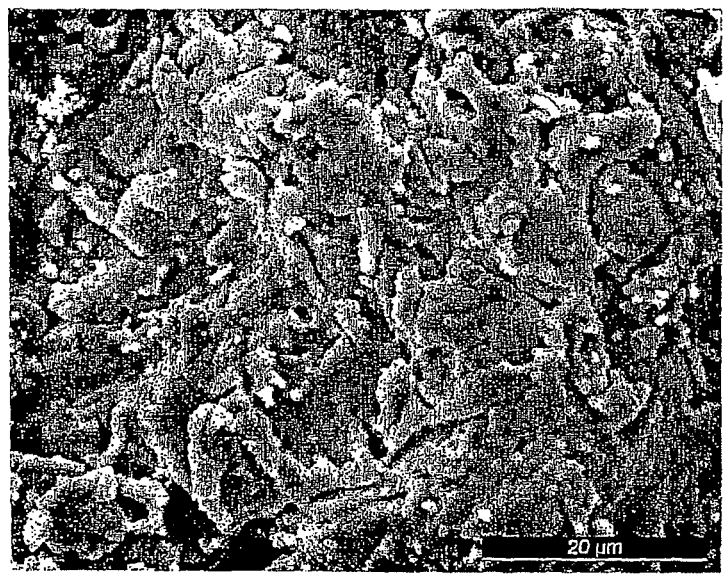
FIG. 5 shows resulting oxidized structured surface of the implant according to example 5.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 360-mesh particle size. Thereafter, the surface of the injected and sintered part was reduced in H2 atmosphere at 1200° C. for 60 min. The surface thus metallized was etched with an acid mixture (50% HCl (32% strength)/25% $H_2SO_4$ (95-97% strength)) at 110° C. for 120 min. The surface thus structured was oxidized at 1200° C. for 140 min. The resulting structured surface of the implant is shown in FIG. 5. The measured roughness values were as follows:

| Sa | Sq | St | Sk | Rt | Rq | Ra |
|---|---|---|---|---|---|---|
| 1.86 | 2.54 | 33.8 | 1.06 | 3.95 | 0.518 | 0.423 |

Example 6

Figure 6:
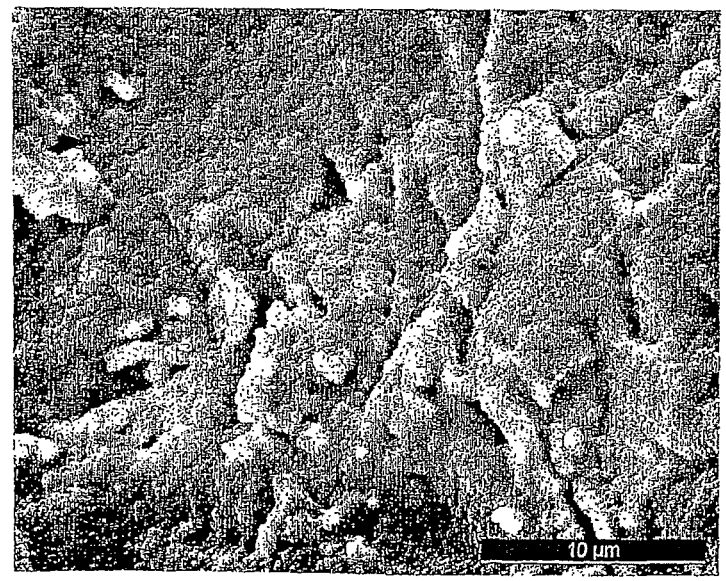
FIG. 6 shows resulting oxidized structured surface of the implant according to example 6.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 360-mesh particle size. Thereafter, the surface of the injected and sintered part was reduced in H2 atmosphere at 1200° C. for 60 min. The surface thus metallized was etched with an acid mixture (50% HCl (32% strength)/25% $H_2SO_4$ (95-97% strength)) at 110° C. for 60 min. The surface thus structured was oxidized at 1200° C. for 140 min. The resulting structured surface of the implant is shown in FIG. 6. The measured roughness values were as follows:

| Sa | Sq | St | Sk | Rt | Rq | Ra |
|---|---|---|---|---|---|---|
| 1.86 | 2.54 | 33.8 | 1.06 | 3.95 | 0.518 | 0.423 |

Example 7

Figure 7:
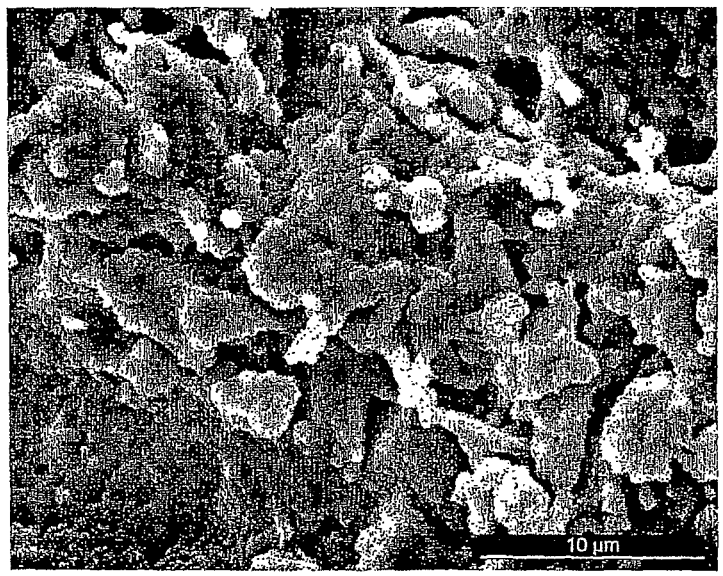
FIG. 7 shows resulting oxidized structured surface of the implant according to example 7.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 360-mesh particle size. Thereafter, the surface of the injected and sintered part was reduced in H2 atmosphere at 1200° C. for 60 min. The surface thus metallized was etched with an acid mixture (50% HCl (32% strength)/25% $H_2SO_4$ (95-97% strength)) at 110° C. for 300 min. The surface thus structured was oxidized at 1200° C. for 140 min. The resulting structured surface of the implant is shown in FIG. 7. The measured roughness values were as follows:

| Sa | Sq | St | Sk | Rt | Rq | Ra |
|---|---|---|---|---|---|---|
| 1.86 | 2.54 | 33.8 | 1.06 | 3.95 | 0.518 | 0.423 |

Example 8

Figure 8:
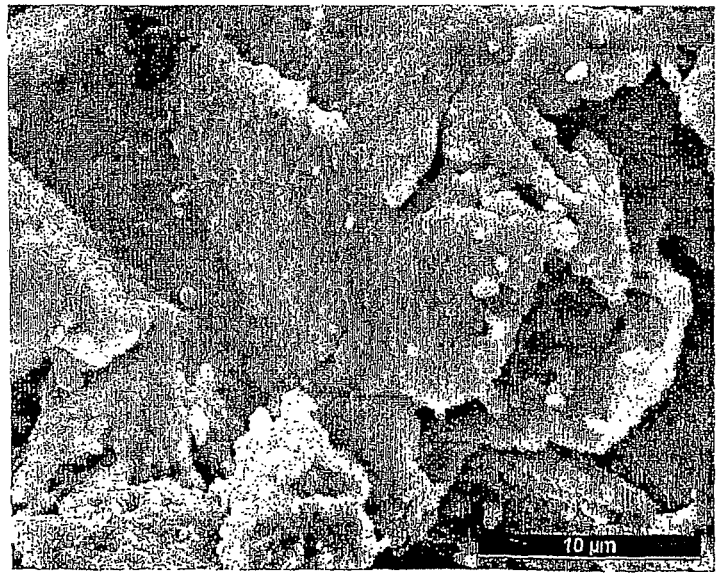
FIG. 8 shows resulting oxidized structured surface of the implant according to example 8.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 360-mesh particle size. Thereafter, the surface of the injected and sintered part was reduced in H2 atmosphere at 1200° C. for 60 min. The surface thus metallized was etched with an acid mixture (50% HCl (32% strength)/25% $H_2SO_4$ (95-97% strength)) at 110° C. for 120 min. The surface thus structured was oxidized at 1200° C. for 140 min. The resulting structured surface of the implant is shown in FIG. 8. The measured roughness values were as follows:

| Sa | Sq | St | Sk | Rt | Rq | Ra |
|---|---|---|---|---|---|---|
| 4.13 | 5.12 | 35.8 | 0.99 | 5.35 | 0.534 | 0.429 |

Example 9

Figure 9:
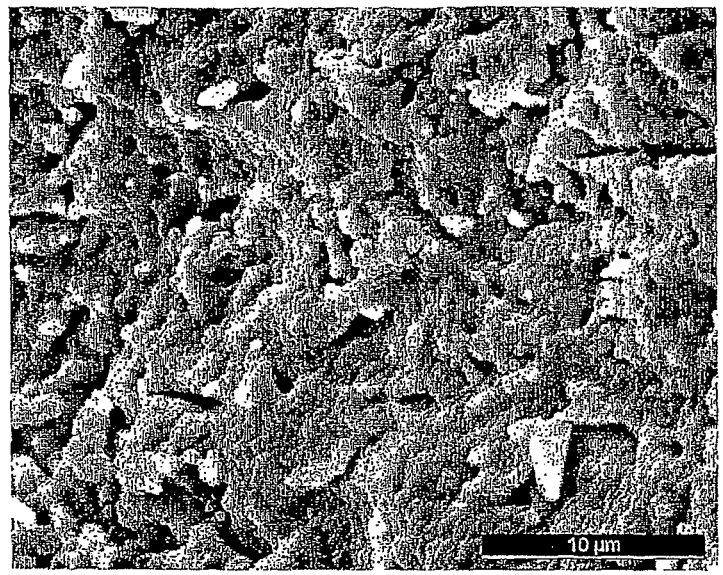
FIG. 9 shows resulting oxidized structured surface of the implant according to example 9.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ having a mixture of 120-mesh and 360-mesh particle size. Thereafter, the surface of the injected and sintered part was reduced in H2 atmosphere at 1200° C. for 60 min. The surface thus metallized was etched with an acid mixture (50% HCl (32% strength)/25% $H_2SO_4$ (95-97% strength)) at 110° C. for min. The surface thus structured was oxidized at 1200° C. for 140 min. The resulting structured surface of the implant is shown in FIG. 9. The measured roughness values were as follows:

| Sa | Sq | St | Sk | Rt | Rq | Ra |
|---|---|---|---|---|---|---|
| 4.13 | 5.12 | 35.8 | 0.99 | 5.35 | 0.534 | 0.429 |

Procedure 2

Reduction of the Ceramic Surface with Graphite During the HIP Process, Etching of the Metallized Surface with a Molten Salt Example 10

Figure 10:
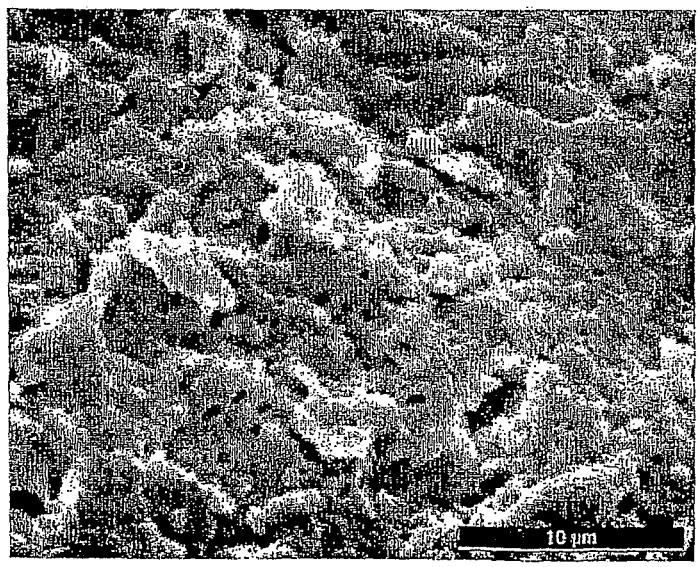
FIG. 10 in a) shows the structured surface of the implant according to example 10 below before oxidation, and in b) the surface oxidized at 1000° C. for 140 min so the resulting structured surface of the oxidized implant.
Figure 10:
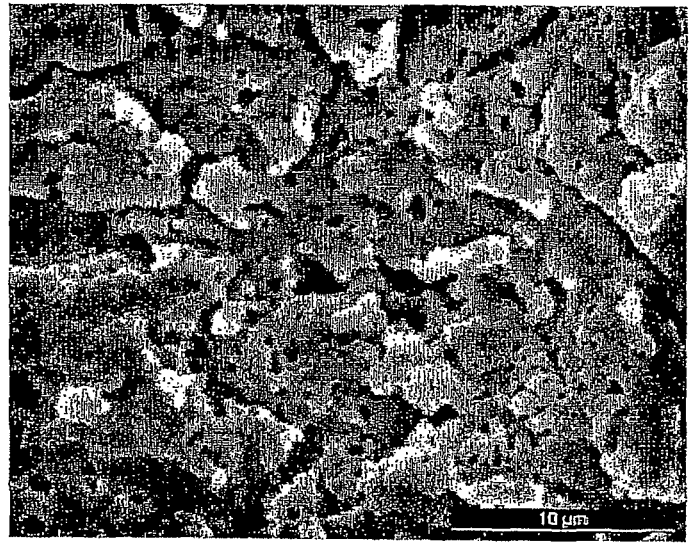

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ having a mixture of 120-mesh and 360-mesh particle size. Thereafter, the surface of the injected and sintered part was reduced by means of graphite in the HIP process at 1400° C. and 1000 bar for 60 min. The surface thus metallized was etched with a molten salt (50% LiOH/50% NaOH) at 200° C. for 30 hours. The resulting structured surface of the still unoxidized implant is shown in FIG. 10a. The surface thus structured was oxidized at 1000° C. for 140 min. The resulting structured surface of the implant is shown in FIG. 10b. The measured roughness values were as follows:

| Sa | Sq | St | Sk | Rt | Rq | Ra |
|---|---|---|---|---|---|---|
| 3.69 | 4.66 | 35 | 1.04 | 4.62 | 0.529 | 0.425 |

Procedure 3

Reduction of the Ceramic Surface with Graphite During the HIP Process, Etching of the Metallized Surface with Acid Example 11

Figure 11:
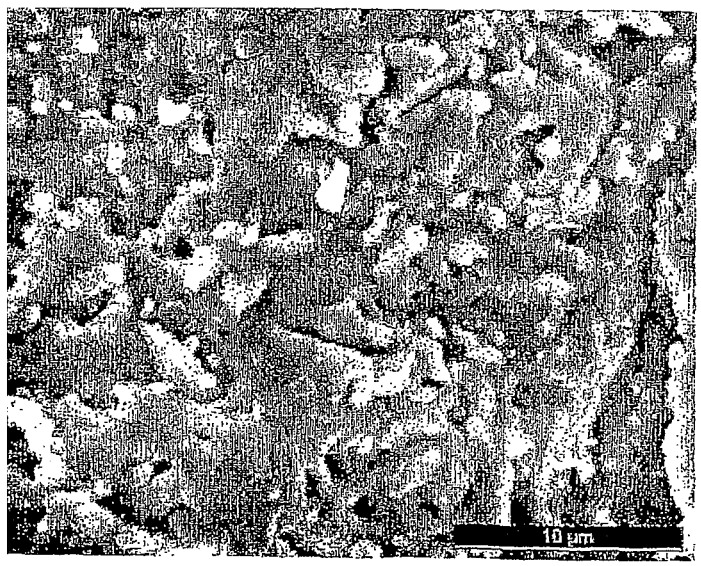
FIG. 11 shows resulting oxidized structured surface of the implant according to example 11.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ having a mixture of 120-mesh and 360-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% $H_2SO_4$ (95-97% strength)) at 110° C. for 30 min. The surface thus structured was oxidized at 1200° C. for 140 min. The resulting structured surface of the implant is shown in FIG. 11. The measured roughness values were as follows:

| Sa | Sq | St | Sk | Rt | Rq | Ra |
|---|---|---|---|---|---|---|
| 4.13 | 5.12 | 35.8 | 0.99 | 5.35 | 0.534 | 0.429 |

Example 12

Figure 12:
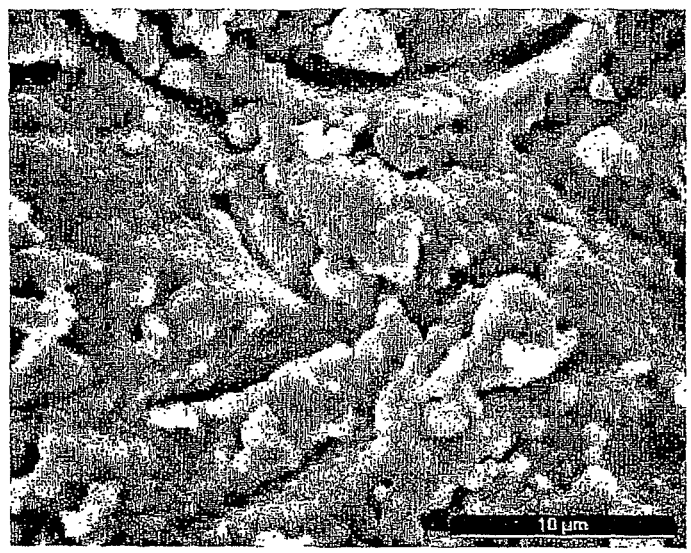
FIG. 12 shows resulting oxidized structured surface of the implant according to example 12.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 360-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% $H_2SO_4$ (95-97% strength)) at 110° C. for 20 min. The surface thus structured was oxidized at 1200° C. for 140 min. The resulting structured surface of the implant is shown in FIG. 12. The measured roughness values were as follows:

| Sa | Sq | St | Sk | Rt | Rq | Ra |
|---|---|---|---|---|---|---|
| 2.35 | 308 | 24.7 | 1.23 | 4.36 | 0.586 | 0.483 |

Example 13

Figure 13:
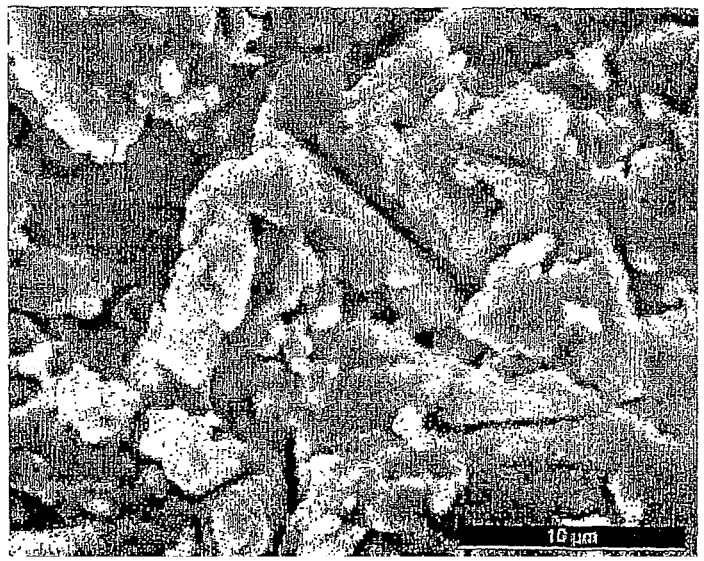
FIG. 13 shows resulting oxidized structured surface of the implant according to example 13.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 360-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% $H_2SO_4$ (95-97% strength)) at 110° C. for 30 min. The surface thus structured was oxidized at 1200° C. for 140 min. The resulting structured surface of the implant is shown in FIG. 13. The measured roughness values were as follows:

| Sa | Sq | St | Sk | Rt | Rq | Ra |
|---|---|---|---|---|---|---|
| 2.35 | 308 | 24.7 | 1.23 | 4.36 | 0.586 | 0.483 |

Example 14

Figure 14:
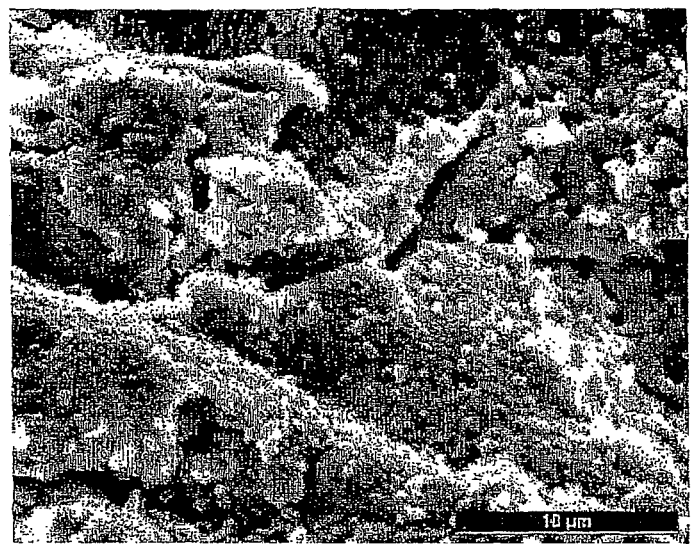
FIG. 14 shows resulting oxidized structured surface of the implant according to example 14.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with $Al_2O_3$ of 120-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% $H_2SO_4$ (95-97% strength)) at 110° C. for 120 min. The surface thus structured was oxidized at 1200° C. for 140 min. The resulting structured surface of the implant is shown in FIG. 14. The measured roughness values were as follows:

| Sa | Sq | St | Sk | Rt | Rq | Ra |
|------|------|------|------|------|-------|-------|
| 4.13 | 5.12 | 35.8 | 0.99 | 5.35 | 0.534 | 0.429 |

Example 15

Figure 15:
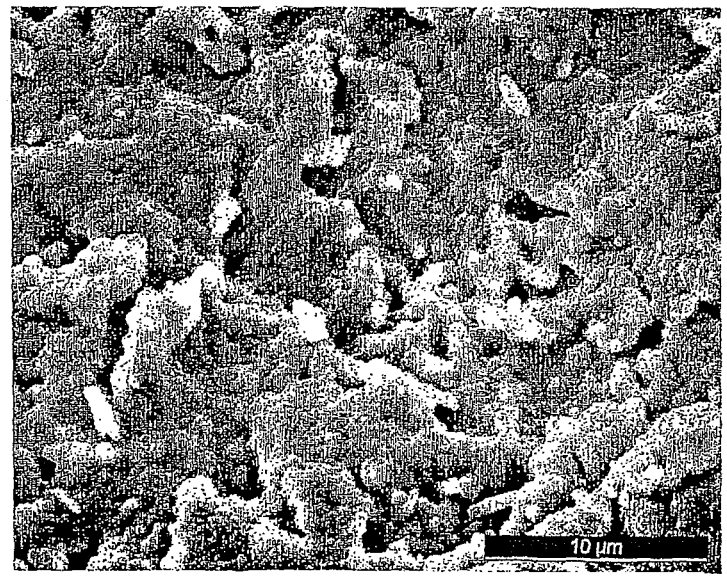
FIG. 15 shows resulting oxidized structured surface of the implant according to example 15.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with Al$_2$O$_3$ having a mixture of 120-mesh and 360-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% H$_2$SO$_4$ (95-97% strength)) at 110° C. for 300 min. The surface thus structured was oxidized at 1200° C. for 140 min. The resulting structured surface of the implant is shown in FIG. 15. The measured roughness values were as follows:

| Sa | Sq | St | Sk | Rt | Rq | Ra |
|------|------|------|------|------|-------|-------|
| 4.13 | 5.12 | 35.8 | 0.99 | 5.35 | 0.534 | 0.429 |

Example 16

Figure 16:
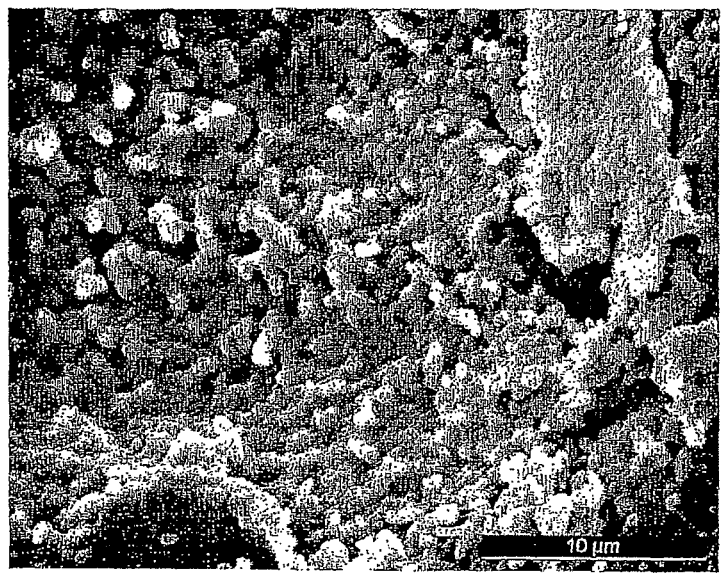
FIG. 16 shows resulting oxidized structured surface of the implant according to example 16.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with Al$_2$O$_3$ of 120-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% H$_2$SO$_4$ (95-97% strength)) at 110° C. for 300 min. The surface thus structured was oxidized at 1200° C. for 140 min. The resulting structured surface of the implant is shown in FIG. 16. The measured roughness values were as follows:

| Sa | Sq | St | Sk | Rt | Rq | Ra |
|------|------|------|------|------|-------|-------|
| 4.13 | 5.12 | 35.8 | 0.99 | 5.35 | 0.534 | 0.429 |

Example 17

Figure 17:
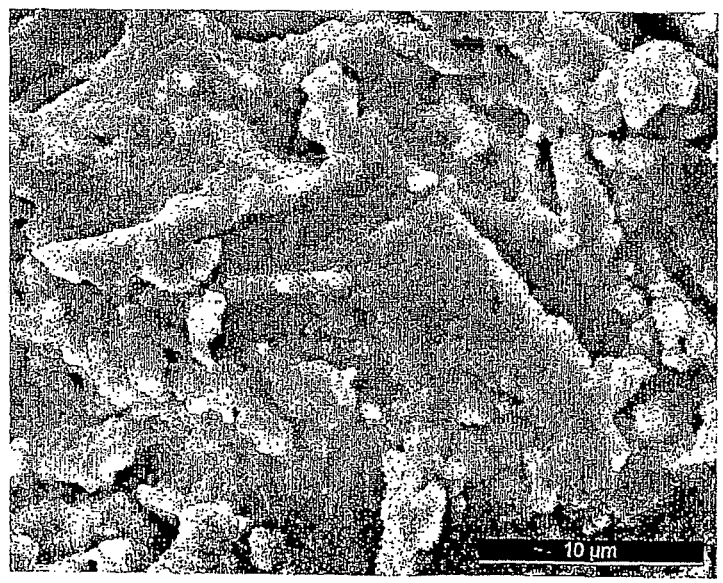
FIG. 17 shows resulting oxidized structured surface of the implant according to example 17.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with Al$_2$O$_3$ of 360-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% H$_2$SO$_4$ (95-97% strength)) at 110° C. for 210 min. The surface thus structured was oxidized at 1200° C. for 140 min. The resulting structured surface of the implant is shown in FIG. 17. The measured roughness values were as follows:

| Sa | Sq | St | Sk | Rt | Rq | Ra |
|------|-----|------|------|------|-------|-------|
| 2.35 | 308 | 24.7 | 1.23 | 4.36 | 0.586 | 0.483 |

Example 18

Figure 18:
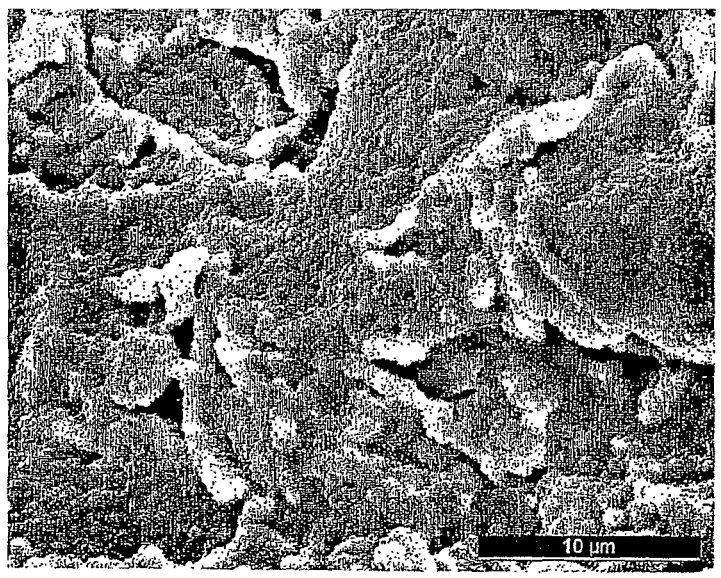
FIG. 18 shows resulting oxidized structured surface of the implant according to example 18.

A green body in the form of a cylindrical tooth implant measuring 10 mm in length and 4 mm in diameter was injected from yttria-stabilized zirconia powder (Y-TZP, CIM process). The injection tool was modified by means of erosion, such that the green body has a macrostructure after the injection. The green body was additionally blasted with Al$_2$O$_3$ of 360-mesh particle size. Thereafter, the surface of the injected and sintered part was reduced by means of graphite in the HIP process at 1400° C. and 1000 bar for 60 min. The surface thus metallized was etched with an acid mixture (50% HCl (32% strength)/25% H$_2$SO$_4$ (95-97% strength)) at 110° C. for 300 min. The surface thus structured was oxidized at 1200° C. for 140 min. The resulting structured surface of the implant is shown in FIG. 18. The measured roughness values were as follows:

| Sa | Sq | St | Sk | Rt | Rq | Ra |
|------|-----|------|------|------|-------|-------|
| 2.35 | 308 | 24.7 | 1.23 | 4.36 | 0.586 | 0.483 |

The invention claimed is:

1. A process for producing a ceramic implant which is structured on a surface, at least in an area exposed to bone and/or tissue, wherein
after the ceramic implant has been shaped, the ceramic implant, in the area to be structured,
I is reduced to a corresponding metal on the surface;
II a substantially metallic surface is then subjected to a structuring surface treatment; and
III the structured surface is oxidized.

2. The process as claimed in claim 1, wherein the ceramic implant is sintered before step I.

3. The process as claimed in claim 2, wherein a preliminary structuring of the surface of the ceramic implant is done prior to steps I-III (1) by surface structuring of a green body before sintering, and/or (2) by using a mold in a shaping step, which the mold is structured on the inside or has spacers, and/or (3) by surface structuring of the sintered ceramic implant.

4. The process as claimed in claim 3, wherein surface structuring of the sintered ceramic implant is performed by an abrasive blasting treatment with simultaneous and/or consecutive treatment with two abrasive blasting agents of different mean grain size.

5. The process as claimed in claim 1, wherein the reduction in step I is carried out under a reducing gas atmosphere.

6. The process as claimed in claim 1, wherein the reduction in step I is carried out using graphite.

7. The process as claimed in claim 1, wherein, in step II, said substantially metallic surface is exposed, in the area to be structured, to a treatment with concentrated acid.

8. The process as claimed in claim 1, wherein, in step II, said substantially metallic surface is subjected, in the area to be structured, to a treatment in a molten salt.

9. The process as claimed in claim 1, wherein, in step III, the surface-structured implant is kept under an oxidizing gas atmosphere.

10. The process as claimed in claim 1, wherein the implant is a ceramic implant based on metal oxide.

11. The process as claimed in claim 1, wherein the implant is structured on the surface at least in the area exposed to a gum.

12. The process as claimed in claim 1, wherein the ceramic implant is already subjected to a structuring of said surface before being shaped and optionally sintered and/or after being shaped and optionally sintered, but before being treated in steps I-III.

13. The process as claimed in claim 2, wherein a preliminary structuring of the surface of the ceramic implant is done, prior to steps I-III, by surface structuring of a green body before sintering, and/or by using a mold in the shaping step, which mold is structured on the inside or has spacers, and/or by surface structuring of the sintered ceramic implant, effected by an abrasive blasting and/or by a chemical treatment with acid, treatment with alkaline solution, and/or treatment with molten salt.

14. The process as claimed in claim 3, wherein said preliminary structuring of the surface is effected by an abrasive blasting treatment with simultaneous and/or consecutive treatment with two abrasive blasting agents of different mean grain size, with a proportion of a coarse grain size in the range of 80-180 mesh and a proportion of a small grain size in the range of 300-450 mesh, and the abrasive blasting agent being sand and/or organic material such as fruit kernels.

15. The process as claimed in claim 1, wherein the reduction in step I is carried out under a reducing gas atmosphere, at a temperature in the range of 1000° C.-1400° C., and/or for a duration in the range of 40 minutes to 20 hours.

16. The process as claimed in claim 15, wherein the reduction in step I is carried out under a hydrogen atmosphere.

17. The process as claimed in claim 1, wherein, in step II, said substantially metallic surface is exposed, in the area to be structured, to a treatment with acid, with the aid of a mixture of hydrochloric acid and/or sulphuric acid and/or nitric acid, the treatment with acid being carried out at a temperature above 100° C., for a duration of in the range of 110-400 minutes.

18. The process as claimed in claim 1, wherein, in step II, said substantially metallic surface is subjected, in the area to be structured, to a treatment in a molten salt, with the aid of alkali metal and/or alkaline earth metal chlorides and/or hydroxides, the treatment in the molten salt being carried out at a temperature above 100° C.

19. The process as claimed in claim 1, wherein, in step III, the surface-structured implant is kept under an oxidizing gas atmosphere, at a temperature in the range of 1000° C.-1500° C., for a duration in the range of 120-600 minutes.

20. The process as claimed in claim 19, wherein, in step III, the surface-structured implant is kept in air.

21. The process as claimed in claim 1, wherein the implant is a ceramic implant based on alumina and/or based on zirconia and/or based on silicon nitride.

22. The process as claimed in claim 1, wherein in step III, the structured surface is again reoxidized.

\* \* \* \* \*